United States Patent
Kühle et al.

[11] B 4,014,923
[45] Mar. 29, 1977

[54] N-CARBOXYLATED N-METHYLCARBAMIC ACID ARYL ESTERS

[75] Inventors: Engelbert Kühle, Bergisch-Gladbach; Peter Siegle, Cologne; Wolfgang Behrenz, Cologne; Ingeborg Hammann, Cologne, all of Germany

[73] Assignee: Bayer Aktiengesellschaft, Leverkusen, Germany

[22] Filed: June 27, 1974

[21] Appl. No.: 483,746

[44] Published under the second Trial Voluntary Protest Program on March 23, 1976 as document No. B 483,746.

Related U.S. Application Data

[62] Division of Ser. No. 265,843, June 23, 1972, Pat. No. 3,857,860.

[30] Foreign Application Priority Data

July 2, 1971   Germany ............................ 2132936

[52] U.S. Cl. .............................................. 260/479 C
[51] Int. Cl.² ...................................... C07C 125/06
[58] Field of Search ................................ 260/479 C

[56] References Cited
UNITED STATES PATENTS

| | | | |
|---|---|---|---|
| 2,599,737 | 6/1952 | Adelson | 260/479 C |
| 3,111,539 | 11/1963 | Bocker et al. | 260/479 C |
| 3,555,076 | 1/1971 | Thoma et al. | 260/479 C |
| 3,657,324 | 3/1972 | Sheppard et al. | 260/479 C |
| 3,789,033 | 1/1974 | Hagemann et al. | 260/479 C |

*Primary Examiner*—James A. Patten
*Attorney, Agent, or Firm*—Burgess, Dinklage & Sprung

[57] ABSTRACT

N-carboxylated N-methylcarbamic acid aryl esters of the general formula

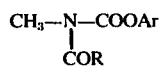

in which Ar is phenyl, naphthyl, dihydrobenzofuranyl or indanyl optionally substituted by alkyl, alkenyl, alkynyl, alkoxy, alkenoxy, alkynoxy, alkylmercapto, alkenylmercapto, alkynylmercapto, dialkylamino, trihalomethyl, halogen, nitro, cyano, cycloalkyl, formamidino, dioxolanyl, dioxanyl or dialkoxymethyl, and R is OAr or optionally substituted alkoxy, alkenoxy, alkynoxy, cycloalkyloxy, amino, alkylmercapto or arylmercapto, which possess insecticidal and acaricidal properties.

4 Claims, No Drawings

N-CARBOXYLATED N-METHYLCARBAMIC ACID ARYL ESTERS

This is a division of application Ser. No. 265,843, filed June 23, 1972, now U.S. Pat. No. 3,857,860 issued Dec. 30, 1974.

The present invention relates to and has for its objects the provision of particular new N-carboxylated N-methylcarbamic acid aryl esters which possess insecticidal and acaricidal properties, active compositions in the form of mixtures of such compounds with solid and liquid dispersible carrier vehicles, and methods for producing such compounds and for using such compounds in a new way especially for combating pests, e.g. insects and acarids with other and further objects becoming apparent from a study of the within specification and accompanying examples.

It is known that N-acylated N-methylcarbamic acid aryl esters possess some insecticidal properties. While the toxicity to warm-blooded animals of these compounds is generally more favorable than that of the carbamates, the insecticidal action of the known N-acylated carbamates is not satisfactory (compare British patent specification No. 982,235).

The present invention provides N-carboxylated N-methylcarbamic acid aryl esters of the general formula

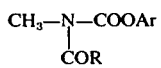     (I)

in which

Ar is phenyl, naphthyl, dihydrobenzofuranyl or indanyl optionally substituted by alkyl, alkenyl, alkynyl, alkoxy, alkenoxy, alkynoxy, alkylmercapto, alkenylmercapto, alkynylmercapto, dialkylamino, trihalomethyl, halogen, nitro, cyano, cycloalkyl, formamidino, dioxolanyl, dioxanyl or dialkoxymethyl, and R is OAr or optionally substituted alkoxy, alkenoxy, alkynoxy, cycloalkyloxy, amino, alkylmercapto or arylmercapto.

Preferably, Ar is phenyl, naphthyl, indanyl or dihydrobenzofuranyl optionally substituted one or more times by a lower alkyl, alkenyl, alkynyl, alkoxy, alkenoxy, alkynoxy, alkylmercapto, alkenylmercapto or alkynylmercapto of up to 4 carbon atoms, or by dimethylamino, trifluoromethyl, chlorine, bromine, fluorine, nitro, cyano, cycloalkyl of 5 or 6 ring carbon atoms substituted with lower alkyl of 1 to 4 carbon atoms, or by N,N-dimethyl- or N-N-diethylformamidino, or by dioxolanyl or dioxanyl optionally substituted by lower alkyl of 1 to 4 carbon atoms, or by a lower dialkoxymethyl radical; and R is optionally substituted lower alkoxy, alkenoxy, alkynoxy or alkylmercapto of 1 to 4 carbon atoms, or —NH₂, aliphatic, cycloaliphatic, heterocyclic or aromatic primary or secondary amino, arylmercapto substituted by lower alkyl of 1 to 4 carbon atoms or chlorine, or OAr as defined herein.

It is distinctly suprising that the compounds according to the invention display a greater insecticidal and acaricidal potency than previously known N-acyl-N-methylcarbamic acid aryl esters. The compounds according to the invention hence represent an enrichment of the art.

Examples of compounds according to the invention include the N-(phenoxycarbonyl)-N-methylcarbamic acid phenyl ester, 2-isopropoxyphenyl ester, 3,5-dimethyl-4-methylmercaptophenyl ester, 3-methyl-4-dimethylaminophenyl ester, 2-cyclopentylphenyl ester, 2-dioxolanylphenyl ester, 2-chlorophenyl ester, 4-tolyl ester, 2-methoxy-4-methylphenyl ester, 4-trifluoromethylphenyl ester, 4-nitrophenyl ester, 2-allyloxyphenyl ester, 4-propargylphenyl ester, 1-naphthyl ester, 7-(2,2-dimethyl-2,3-dihydrobenzofuranyl) ester, 3-dimethylformamidinophenyl ester, methyl ester, isopropyl ester, sec. butyl ester, methallyl ester, propargyl ester, amide, dimethylamide, allylamide, dodecylamide, cyclohexylamide, anilide, 4-chloroanilide, 3-nitroanilide, 4-aniside, morpholide and 2-pyridylamide; N-(2-isopropoxyphenylcarbonyl)-N-methylcarbamic acid 2-isopropoxyphenyl ester, 3,5-dimethyl-4-methylmercaptophenyl ester, 2-cyclopentylphenyl ester, thiomethyl ester, thiobutyl ester, thiophonyl ester, 4-chlorothiophenyl ester, dimethylamide, allyl ester, 2-chloroethyl ester, 2-methoxyethyl ester, 2-diethylaminoethyl ester and 2-ethylmercaptoethyl ester; N-(3-methyl-4-dimethylaminophenoxycarbonyl)-N-methylcarbamic acid 2-chlorophenyl ester, 2-dioxolanylphenyl ester, 2-isopropylphenyl ester, methylamide, diallylamide, cyclopentyl ester, benzyl ester and 4-nitrobenzyl ester; N-(1-naphthoxycarbonyl)-N-methylcarbamic acid 2-methoxyphenyl ester, ethyl ester, propargyl ester and isopropyl ester; N-(7-(2,2-dimethyl-2,3-dihydrobenzofuranoxy))-N-methylcarbamic acid 2-dioxolanylphenyl ester, butyl ester, isopropylamide, thioethyl ester, and thio-4-methylphenyl ester.

The invention also provides a process for the production of an N-carboxylated N-methylcarbamic acid aryl ester of the formula (I) in which a. an N-chlorocarbonyl-N-methylcarbamic acid aryl ester of the general formula

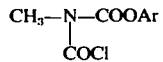     (II)

in which

Ar has the abovementioned meaning, is reacted with a compound of the general formula

HR     (III)

in which

R has the abovementioned meaning, in the form of a salt or in the presence of an acid-binding agent, and in the presence of a diluent, or b. a compound of the general formula

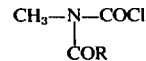     (IV)

in which

R has the abovementioned meaning, is reacted with a phenol of the formula

ArOH     (V)

in which

Ar has the abovementioned meaning, in the form of a salt or in the presence of an acid-binding agent, and in the presence of a diluent.

If in reaction (a) N-chlorocarbonyl-N-methylcarbamic acid phenyl ester and 2-isopropoxyphenol are used as the starting substances, the course of the reaction can be represented by the following formula scheme:

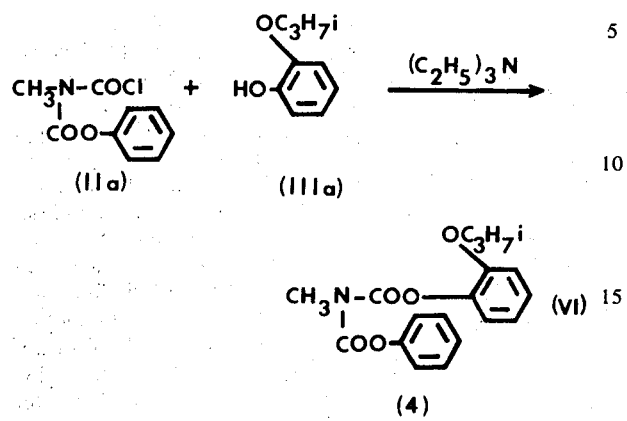

Some of the N-chlorocarbonyl-N-methylcarbamic acid aryl esters are known. These compounds can be prepared either by phosgenation of appropriate N-methylcarbamic acid aryl esters according to DAS (German published specification) No. 1,259,871or by reaction of the known bis-chlorocarbonyl-methylamine (compare Organic Synthesis 1970, 542) with a phenol.

The phenols or aroxy compounds required for the reaction, defined by the formulas (II) and (V), are known.

The diluent may for example be any inert organic solvent. These include others, such as diethyl ether, tetrahydrofuran and dioxane, hydrocarbons, such as benzene, and chlorinated hydrocarbons, such as chloroform and chlorobenzene. The reaction can alternatively be carried out in water, or in an excess of a compound RH of the formula (III) for example methanol, butanol or cyclohexanol as the diluent.

In order to bind any hydrogen chloride produced during the reaction, a tertiary base, such as triethylamine, or an inorganic base, such as an alkali metal hydroxide or alkali metal carbonate, may be added to the reaction mixture. Alternatively, it is possible to start from a salt of the compound RH, especially an alkali metal salt, such as an alkali metal phenolate, alkali metal alcoholate or alkali metal mercaptide.

The reaction temperatures can be varied over a wide range; in general, the reaction is carried out at from about 0° to 100°C, preferably at about 20° to 40°C.

In carrying out the process according to the invention, equimolar amounts may in general be used. In many cases it has proved advantageous if the compound RH of the formula (III) is employed in an excess of up to about 100%, preferably up to about 20%.

To the sucking insects contemplated herein there belong, in the main, aphids (Aphidae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korscnelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Climex lectularius*), the assassin bug (*Rhodnius prolixus*) and Chagas' bug (*Triatoma infestans*) and, further, cicadas, such as *Euscelis bilobatus* and *Nephotettix bipunctatus;* and the like.

In the case of the biting insects contemplated herein, above all there should be mentioned butterfly caterpillars (Lepidoptera) such as the diamond-back moth (*Plutella maculipennis*), the gypsy moth (*Lymantria dispar*), the browntail moth (*Euproctis chrysorrhoea*) and tent caterpillar (*Malacosoma neustria*); further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuhniella*) and greater wax moth (*Galleria mellonella*); and the like.

Also to be classed with the biting insects contemplated herein are bettles (Coleoptera), for example the granary weevil (*Sitophilus granarius = Calandra granaria*), the Colorado beetle (*Leptinotarsa decemlineata*), the dock bettle (*Gastrophysa viridula*), the mustard beetle (*Phaedon cochleariae*), the blossom beetle (*Meligethes aeneus*), the raspberry bettle (*Byturus tomentosus*), the bean weevil (*Bruchidius = Acanthoscelides obtectus*), the leather bettle (*Dermestes frischi*), the khapra bettle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cochroaches, such as the German cockroach (*Blattella germanica*), American cockroach (*Periplaneta americana*), Madeira cockroach (Leucophaea or Rhyparobia maderae), oriental cockroach (*Blatta orientalis*), the giant cockroach (*Blaberus giganteus*) and the black giant cockroach (*Blaberus fuscus*) as well as *Henschoutedenia flexivitta;* further, Orthoptera, for example the house cricket (*Acheta domesticus*); termites such as the eastern subterranean termite (*Reticulitermes flavipes*) and Hymenoptera such as ants, for example the garden ant (*Lasius niger*); and the like.

The Diptera contemplated herein comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*); and the like.

With the mites (Acari) contemplated herein there are classed, in particular, the spider mites (Tetranychidae) such as the two-spotted spider mite (*Tetrancyhus telarius = Tetranychus althaeae* or *Tetranychus urticae*) and the European red mite (*Paratetranychus pilosus = Panonychus ulmi*), gall mites, for example the black currant gall mite (*Eriophyes ribis*) and tarsonemids, for example the broad mite (*Hemitarsonemus latus*) and the cyclamen mite (*Tarsonemus pallidus*);

finally, ticks, such as the relapsing fever tick (*Ornithodorus moubata*); and the like.

When applied against hygiene pests and pests of stored products, particularly flies and mosquitoes, the compounds of the invention are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usuable in conventional pesticide formulations or compositions, e.g. conventional pesticide dispersible carrier vehicles such as gases, solutions, emulsions, suspensions, emulsifiable concentrates, spray powders. pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol,, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, moritomorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides and acaricides, or rodenticides fungicides, bactericides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–10%, preferably 0.01–1%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contenplates methods of selectively killing, combating or controlling pests, e.g. insects and acarids, which comprises applying to at least one of correspondingly (a) such insects, (b) such acarids, and (c) the corresponding habitat thereof, i.e. the locus to be protected, a correspondingly combative or toxic amount, i.e. an insecticidally or acaricidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, and the like.

It will be realized, or course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

(1) 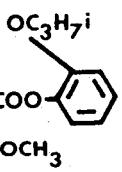

17 g of N-(chlorocarbonyl)-N-methylcarbamic acid 2-isopropoxyphenyl ester and 10 ml of methanol are dissolved in 70 ml of dioxane and the mixture is heated to the boil for 1 hour. In the course thereof, HCl is continuously evolved. After cooling, the solution is concentrated in vacuo and the reaction product is distilled. 11 g of the above compound, of boiling point$_{0.15}$ 155°–160°; $n_D^{20}$: 1.5047, are obtained.

EXAMPLES 2 and 3

The following are obtained analogously to Example 1:

(2) 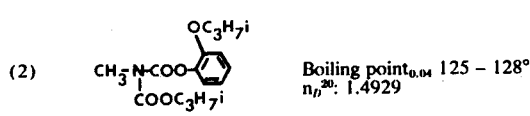 Boiling point$_{0.04}$ 125 – 128° $n_D^{20}$: 1.4929

(3) 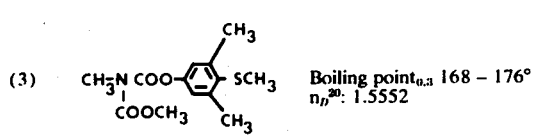 Boiling point$_{0.3}$ 168 – 176° $n_D^{20}$: 1.5552

EXAMPLE 4

(4) 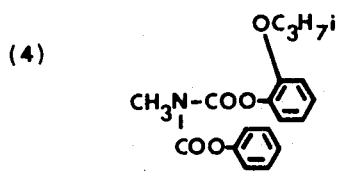

13.5 g of N-(chlorocarbonyl)-N-methylcarbamic acid 2-isopropoxyphenyl ester and 4.7 g of phenol are dissolved in 100 ml of toluene and 7 ml of triethylamine are added at room temperature. In the course thereof, the temperature rises to about 40°. The triethylamine hydrochloride (6.5 g) is filtered off cold, the filtrate is concentrated in vacuo and the residue is distilled. 15 g of the above compound of boiling point$_{0.04}$ 173°–178°; $n_D^{20}$: 1.5412, are obtained.

EXAMPLES 5–8

The following are obtained analogously to Example 4:

(5) 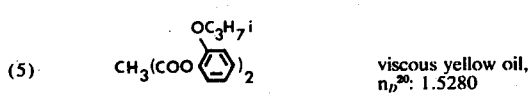 viscous yellow oil, $n_D^{20}$: 1.5280

(6) 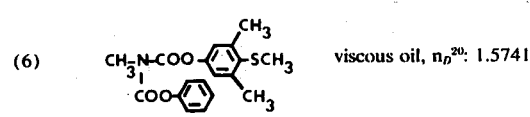 viscous oil, $n_D^{20}$: 1.5741

(7) 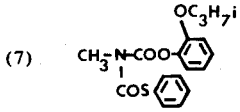 boiling point$_{0.04}$: 180 – 183° $n_D^{20}$: 1.5738

(8) 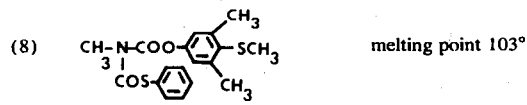 melting point 103°

EXAMPLE 9

(9) 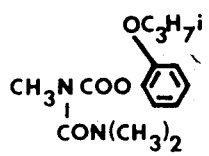

About 5 g of dimethylamine are passed into a solution of 10 g of N-(chlorocarbonyl)-N-methylcarbamic acid 2-isopropoxyphenyl ester in 100 ml of toluene. In the course thereof, the temperature rises to 45°. The amine hydrochloride is filtered off cold and the filtrate is concentrated in vacuo. 9.5 g of the above product are left as the residue, in the form of a viscous oil of $n_D^{20}$: 1.5152.

EXAMPLE 10

(a)  (IVa)

46.8 g of bis-(chlorocarbamyl)-methylamine are first introduced into 200 ml of benzene. 17.4 g of allyl alcohol and 30 g of triethylamine, both diluted with benzene to the same volume, are slowly added dropwise simultaneously. The reaction is strongly exothermic and the temperature is kept below 40°C by cooling. Thereafter the amine hydrochloride is filtered off, the solution is concentrated and the reaction product N-chlorocarbamyl-N-methylcarbamic acid allyl ester, is distilled off in vacuo: boiling point $_{0.1}$ = 80°–82°C; $n_D^{20}$: 1.4728.

(b)
(10) 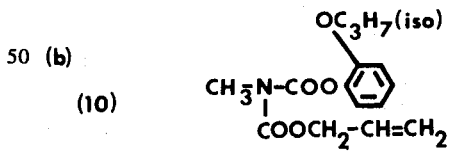

17.8 g of N-chlorocarbonyl-N-methylcarbamic acid allyl ester and 15.2 g of C-isopropoxyphenol are dissolved in 200 ml of benzene and 11 g of triethylamine are added at room temperature. The reaction is exothermic. After 2 hours, the triethylamine hydrochloride is filtered off cold and the benzene phase is twice washed with water. After drying with Na$_2$SO$_4$, the solvent is distilled off. A yellow oil remains (20g); $n_D^{20}$: 1.5850.

EXAMPLES 11–14

The following are obtained analogously to the above Examples:

(11) 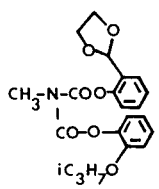 melting point 72 – 73°

(12) 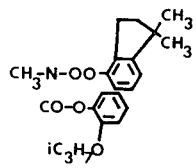 viscous oil $n_D^{20} = 1.5385$

(13) 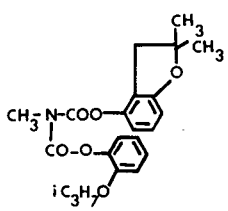 viscous oil

(14) 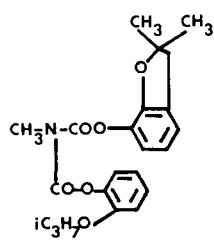 melting point = 76 – 77°

In the following comparative biological examples Comparison agent A has the following formula:

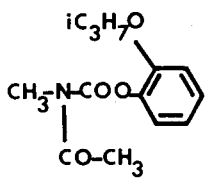

EXAMPLE 15

$LD_{100}$ test
Test insects: *Aedes aegypti*
Solvent: acetone 2 parts by weight of the active compound are dissolved in 1000 parts by volume of the solvent. The solution so obtained is diluted with further solvent to the desired concentrations.

2.5 ml of the solution of the active compound are pipetted into a Petri dish. On the bottom of the Petri dish there is a filter paper with a diameter of about 9.5 cm. The Petri dish remains uncovered until the solvent has completely evaporated. The amount of active compound per square meter of filter paper varies with the concentration of the solution of active compound used. About 25 test insects are then placed in the Petri dish and it is covered with a glass lid.

The condition of the test insects is observed after the commencement of the experiments. The destruction is determined as a percentage.

The active compounds, the concentrations of the active compounds, the test insects and the results can be seen from the following Table 1:

Table 1

| Active Compounds | $LD_{100}$ Test Active Compound Concentrations % strength solution | Destruction in % |
| --- | --- | --- |
| Comparison agent A: | 0.2 | 100 |
|  | 0.04 | 100 |
|  | 0.008 | 100 |
|  | 0.0016 | 100 |
|  | 0.00032 | 10 |
| According to the invention: | 0.2 | 100 |
|  | 0.04 | 100 |
| 10 | 0.008 | 100 |
|  | 0.0016 | 100 |
|  | 0.00032 | 100 |

EXAMPLLE 16

$LT_{100}$ test
Test insects: *Blattella germanica* (females)
Solvent: acetone 2 parts by weight of the active compound are dissolved in 1000 parts by volume of the solvent. The solution so obtained is diluted with further solvent to the desired concentrations.

2.5 ml of the solution of the active compound are pipetted into a Petri dish. On the bottom of the Petri dish there is a filter paper with a diameter of about 9.5 cm. The Petri dish remains uncovered until the solvent has completely evaporated. The amount of active compound per square meter of filter paper varies with the concentration of the solution of active compound used. About 25 test insects are then placed in the Petri dish and it is covered with a glass lid.

The condition of the test insects is observed 3 days after the commencement of the experiments. The timem after which 100% of the insects are killed is determined.

The active compounds, the concentrations of the active compounds, the test insects and the results can be seen from the following Table 2.

Table 2

| Active Compounds | $LT_{100}$ Test Active Compound Concentrations, % strength solution | $LT_{100}$ |
| --- | --- | --- |
| Comparison agent A: | 0.2 | 150' |
|  | 0.04 | 72 hrs. = 20% |
| According to the invention: | 0.2 | 60' |
|  | 0.04 | 120' |
| 11 | 0.008 | 72 hrs. = 60% |
| 12 | 0.2 | 90' |
|  | 0.04 | 72 hrs. = 80% |
| 9 | 0.2 | 90' |
|  | 0.04 | 6 hrs. |
|  | 0.008 | 72 hrs. = 20% |

EXAMPLE 17

$LT_{100}$ test
Test insects: *Sitophilus granarius*
Solvent: acetone 2 parts by weight of active compound are dissolved in 1000 parts by volume of solvent. The solution so obtained is diluted with further solvent to the desired concentrations.

2.5 ml of the solution of active compound are pipetted into a Petri dish. On the bottom of the Petri dish there is a filter paper with a diameter of about 9.5 cm. The Petri dish remains uncovered until the solvent has completely evaporated. The amount of active compound per square meter of filter paper varies with the concentration of the solution of active compound used. About 25 test insects are then placed in the Petri dish and it is covered with a glass lid.

The condition of the test insects is continuously observed for up to 8 hours. The time which is necessary for a 100% knock down effect is determined.

The active compounds, the concentrations of the active compounds, test insects and results can be seen from the following Table 3:

Table 3

| Active Compounds | $LT_{100}$ Test Active Compound Concentrations % strength solution | $LT_{100}$ |
|---|---|---|
| Comparison agent A: | 0.2 | 90' |
| | 0.04 | 150' |
| | 0.008 | 72 hrs = 10% |
| According to the invention: | | |
| 11 | 0.2 | 90' |
| | 0.04 | 120' |
| | 0.008 | 24 hrs. |

EXAMPLE 18

Test insects: Mosquito larvae
Solvent: 99 parts by weight of acetone
Emulsifier: 1 part by weight of benzylhydroxydiphenyl-polyglycol-ether To produce a suitable preparation of active compound, 2 parts by weight of the active compound are dissolved in 1000 parts by volume of the solvent containing the amount of emulsifier stated above. the solution thus obtained is diluted with water to the desired lower concentrations.

The aqueous preparations of the active compounds are placed in glass vessels and about 25 mosquito larvae are then placed in each glass vessel.

After 24 hours, the degree of destruction is determined as a percentage. 100% means that all the larvae are killed. 0% means that no larvae at all are killed.

The active compounds, the concentrations of the active compounds, the test insects and the results can be seen from the following Table:

Table 4

| Active Compound | Mosquito Larvae Test Active Compound Concentration of the solution in ppm | Degree of destruction in % |
|---|---|---|
| Comparison agent A: | 10 | 100 |
| | 1 | 0 |
| According to the invention: | | |
| 13 | 10 | 100 |
| | 1 | 100 |
| 12 | 10 | 100 |
| | 1 | 100 |
| 5 | 10 | 100 |
| | 1 | 100 |
| 7 | 10 | 100 |
| | 1 | 50 |
| 14 | 10 | 100 |
| | 1 | 100 |

EXAMPLE 19

Residual test

Test insects: Musca domestica and Aedes aegypti
Wettable powder base consisting of:
3 % sodium diisobutylnaphthalene-1-sulfonate
6 % sulfite waste liquor, partially condensed with aniline
40 % highly dispersed silicic acid (containing CaO)
51 % colloidal kaolin To produce a suitable preparation of the active compound, 1 part by weight of the active compound is intimately mixed with 9 parts by weight of the wettable powder base. The spray powder thus obtained is suspended in 90 parts of water.

The suspension of the active compound is sprayed, in an amount of 2 g of the active compound per square meter, on to substrates consisting of different materials.

The sprayed coatings are, at specific intervals of time, tested for their biological activity, until a 100% effect can no longer be found.

For this purpose, the test insects are placed on the treated substrates. There is put over the test insects a squat cylinder which is closed at its upper end with a wire mesh in order to prevent the insects from escaping. After the insects have spent 8 hours on the substrate, the destruction of the test insects is determined as a percentage.

The active compounds, the nature of the test substrates and the results can be seen from the following Table 5.

Table 5

| Active Compounds | Test Substrates | Residual Test Test insects | Destruction of the Test insects in % Age of the residual coatings in weeks | | | | | | | | |
|---|---|---|---|---|---|---|---|---|---|---|---|
| | | | 1 | 2 | 3 | 4 | 6 | 8 | 12 | 16 | 20 |
| Comparison agent A: | Plywood | Musca domestica | 100 | 100 | 80 | — | — | — | — | — | — |
| According to the invention: | | | | | | | | | | | |
| 5 | Plywood | Musca domestica | 100 | 100 | 100 | 100 | 100 | 100 | 100 | 90 | — |
| 2 | Plywood | Musca domestica | 100 | 100 | 100 | 100 | 100 | 100 | 90 | — | — |
| 4 | Plywood | Musca domestica | 100 | 100 | 100 | 100 | 100 | 100 | 100 | 100 | 90 |
| 7 | Plywood | Musca domestica | 100 | 100 | 100 | 100 | 100 | 100 | 90 | — | — |
| 8 | Plywood | Musca domestica | 100 | 100 | 100 | 100 | 100 | 100 | 90 | — | — |
| Comparison agent: | Limed clay | Aedes aegypti | 30 | — | — | — | — | — | — | — | — |
| (B) | Limed clay | Aedes aegypti | 100 | 70 | — | — | — | — | — | — | — |
| (known) According to the invention: | | | | | | | | | | | |
| 5 | Limed clay | Aedes aegypti | 100 | 100 | 100 | 100 | 90 | — | — | — | — |
| 7 | Limed clay | Aedes aegypti | 100 | 100 | 100 | 100 | 100 | 100 | 100 | 90 | — |
| 8 | Limed clay | Aedes aegypti | 100 | 100 | 100 | 30 | — | — | — | — | — |

EXAMPLE 20

Phaedon larvae test

Solvent: 3 parts by weight dimethyl formamide
Emulsifier: 1 part by weight alkylaryl polyglycol ether To produce a suitable preparation of active compound, 1 part by weight of the active compound is mixed with the stated amount of solvent containing the stated amount of emulsifier, and the concentrate is diluted with water to the desired concentration.

Cabbage leaves (*Brassica oleracea*) are sprayed with the preparation of the active compound until dripping wet and then infested with mustard bettle larvae (*Phaedon cochleariae*).

After the specified periods of time, the degree of destruction is determined as a percentage: 100% means that all the beetle larvae are killed. 0% means that none of the beetle larvae are killed.

The active compounds, the concentration of the active compounds, the times of evaulation and the results can be seen from the following Table 6:

Table 6

| | (Insects which are harmful to plants) Phaedon larvae test | |
|---|---|---|
| Active compounds | Active compound concentration in % | Degree of destruction in % after 3 days |
| Comparison agent A: | | |
| | 0.2 | 100 |
| | 0.02 | 0 |
| 4 | 0.2 | 100 |
| | 0.02 | 80 |
| 11 | 0.2 | 100 |
| | 0.02 | 100 |
| 12 | 0.2 | 100 |
| | 0.02 | 90 |
| 13 | 0.2 | 100 |
| | 0.02 | 100 |
| | 0.002 | 50 |
| 3 | 0.2 | 100 |
| | 0.02 | 100 |
| | 0.002 | 100 |
| 8 | 0.2 | 100 |
| | 0.02 | 100 |
| | 0.002 | 100 |
| | 0.0002 | 50 |
| 6 | 0.2 | 100 |
| | 0.02 | 100 |
| | 0.002 | 100 |
| 14 | 0.2 | 100 |
| | 0.02 | 100 |
| | 0.002 | 50 |

EXAMPLE 21

Doralis test (systemic action)

Solvent: 3 parts by weight dimethyl formamide
Emulsifier: 1 part by weight alkylarylpolyglycol ether To produce a suitable preparation of active compound, 1 part by weight of the active compound is mixed with the stated amount of solvent containing the stated amount of emulsifier, and the concentrate is diluted with water to the desired concentration.

Bean plants (*Vicia faba*) which have been heavily infested with the bean aphid (*Doralis fabae*) are watered with the preparation of the active compound so that the preparation of the active compound penetrates into the soil without wetting the leaves of the bean plants. The active compound is taken up by the beam plants from the soil and thus reaches the infested leaves.

After the specified period of time, the degree of destruction is determined as a percentage. 100% means that all the aphids are killed; 0% means that none of the aphids are killed.

The active compounds, the concentrations of the active compounds, the evaluation time and the results can be seen from the following Table 7:

Table 7

| | (Insects which are harmful to plants) Doralis test (systemic action) | |
|---|---|---|
| Active compounds | Active compound concentration in % | Degree of destruction in % after 4 days |
| Comparison agent A: | | |
| | 0.2 | 100 |
| | 0.02 | 40 |
| According to the invention: | | |
| 4 | 0.2 | 100 |
| | 0.02 | 100 |
| 11 | 0.2 | 100 |
| | 0.02 | 100 |
| | 0.002 | 50 |
| 13 | 0.2 | 100 |
| | 0.02 | 100 |
| 9 | 0.2 | 100 |
| | 0.02 | 100 |
| 14 | 0.2 | 100 |
| | 0.02 | 100 |

It will be appreciated that the instant specification and examples are set forth by way of illustration and not limitation, and that various modifications and changes may be made without departing from the spirit and scope of the present invention.

What is claimed is:

1. An N-carboxylated N-methylcarbamic acid aryl ester of the formula $$CH_3-\underset{\underset{COR}{|}}{N}-COOAr$$

in which

Ar is phenyl, naphthyl, or phenyl or naphthyl substituted one or more times by a lower alkyl, alkenyl, alkynyl, alkoxy, alkenoxy, alkynoxy, alkylmercapto, alkenylmercapto or alkynylmercapto each of up to 4 carbon atoms, or by dimethylamino, trifluoromethyl, chlorine, bromine, fluorine nitro, cyano, cycloalkyl of 5 or 6 ring carbon atoms substituted with lower alkyl of 1 to 4 carbon atoms, or by N,N-dimethyl- or N,N-diethylformamidino, or by a lower dialkoxymethyl radical; and R is optionally substituted lower alkoxy, alkenoxy, alkynoxy or alkylmercapto each with 1 to 4 carbon atoms, or anilino, chloranilino, nitroanilino, methoxy anilino, or —NR′$_2$ wherein R′ is individually selected from the group consisting of hydrogen and alkyl, alkenyl, cycloalkyl or cycloalkenyl each of up to 12 carbon atoms, phenylmercapto or phenylmercapto substituted by lower alkyl of 1 to 4 carbon atoms or chlorine, or OAr.

2. The compound according to claim 1 wherein such compound is N-phenoxycarbonyl-N-methylcarbamic acid 2-isopropoxyphenyl ester of the formula (4)

3. The compound according to claim 1 wherein such compound is N-(2-isopropoxyphenoxycarbonyl)-N-methylcarbamic acid 2-isopropoxyphenyl ester of the formula
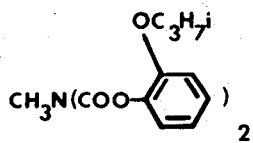
(5)
4. The compound according to claim 1 wherein such compound is N-allyloxycarbonyl-N-methylcarbamic acid 2-isopropoxyphenyl ester of the formula
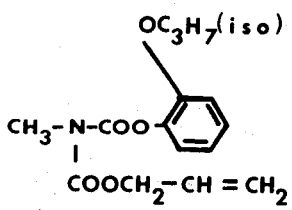
(10)
* * * * *